United States Patent [19]

Bellos

[11] Patent Number: 4,569,785

[45] Date of Patent: Feb. 11, 1986

[54] THIOUREYLENES AND USES THEREOF

[75] Inventor: Thomas J. Bellos, Kirkwood, Mo.

[73] Assignee: Petrolite Corporation, St. Louis, Mo.

[21] Appl. No.: 639,562

[22] Filed: Oct. 29, 1984

Related U.S. Application Data

[62] Division of Ser. No. 170,326, Jul. 21, 1980, Pat. No. 4,492,658.

[51] Int. Cl.$^4$ .................. B01D 17/04; B01D 19/04
[52] U.S. Cl. ................................. 252/344; 252/358; 210/708
[58] Field of Search ............ 252/338, 344, 358; 210/708; 252/8.55 D

[56] References Cited

U.S. PATENT DOCUMENTS

| | | | |
|---|---|---|---|
| 2,284,637 | 6/1942 | Catlin | 260/455 A |
| 3,468,818 | 9/1969 | Phillips | 252/338 X |
| 3,509,046 | 4/1970 | Annand et al. | 210/708 |
| 4,182,690 | 1/1980 | Suzuki et al. | 252/344 X |

FOREIGN PATENT DOCUMENTS 900788 6/1960 United Kingdom ........... 260/455 A

*Primary Examiner*—John F. Terapane
*Assistant Examiner*—Catherine S. Kilby
*Attorney, Agent, or Firm*—Robert E. Wexler

[57] ABSTRACT

This invention relates to Thioureylene prepared by reacting an oxyalkylated polyamine with thiourea and to uses of such Thioureylene for example in removing oils, solids, and combinations thereof from aqueous systems, etc.

15 Claims, No Drawings

THIOUREYLENES AND USES THEREOF

This is a division of application Ser. No. 170,326, filed July 21, 1980, now U.S. Pat. No. 4,492,658.

This invention relates to thioureylenes prepared by reacting an oxyalkylated polyamine with thiourea; and to uses thereof, for example, in removing oils, solids and combinations thereof, etc., from aqueous systems.

Theoretically, when a polyamine reacts with urea the following reactions occur:

$$NH_2-R-NH_2 + NH_2-\overset{\overset{S}{\|}}{C}-NH_2 \xrightarrow[-NH_3]{\Delta T}$$

$$NH_2-R-NH\overset{\overset{S}{\|}}{C}NH_2 \xrightarrow[-NH_3]{\Delta T} \left[R-NH-\overset{\overset{O}{\|}}{C}-NH\right]_n$$

aminoalkylene thioureas     polyalkylene thioureas

Aminoalkylene thiourea and polyalkylene thioureas are also called thioureylenes.

Theoretically, where alcohol reacts with thiourea the following reaction occurs $$ROH + NH_2-\overset{\overset{S}{\|}}{C}-NH_2 \xrightarrow[-NH_3]{\Delta T} RO\overset{\overset{S}{\|}}{C}-NH_2.$$

thiourethanes

I have now discovered that when oxyalkylated polyamines are reacted with thiourea, they yield products which have a wide variety of uses. In general, these compositions are thioureylenes (i.e., aminoalkylene thioureas and polyalkylenethioureas) containing thiourethane groups. They may be linear, contain dangling groups, be crosslinked, or combinations thereof, etc.

Theoretically, wherein the polyamine is bifunctional, a linear polymer is formed; where the polyamine is polyfunctional a cross-linked polymer is formed; where a functional group reacts with a non-polymer such as thiourea, a dangling group is formed, etc.

Ideally stated, the reaction of the oxyalkylated amine may be stated $$\left[NH_2-R-NH_2\right]-(AO)_nH + NH_2\overset{\overset{S}{\|}}{C}NH_2 \xrightarrow[-NH_3]{\Delta T}$$

$$\left[NH_2-R NH\overset{\overset{S}{\|}}{C}-NH_2\right]-(AO)_nH \longrightarrow$$

$$\left[R-NH\overset{\overset{S}{\|}}{C}-NH\right]-(AO)_nH \xrightarrow[-NH_3]{\Delta T}$$

$$\left[R-NH-\overset{\overset{S}{\|}}{C}-NH\right]-(AO)_n\overset{\overset{S}{\|}}{C}NH_2$$

The $-(AO)_nH$ symbolically represents a nitrogen-bonded oxyalkyl group for example $-N-(CH_2CH_2O)_nH$.

A specific illustration is $$\left[R-NH-\overset{\overset{S}{\|}}{C}-\underset{\underset{CH_2CH_2OH}{|}}{N}-\right]$$

and as the thiourethane $$\left[R-\overset{H}{N}-\overset{\overset{S}{\|}}{C}-\underset{\underset{CH_2CH_2O\overset{\overset{S}{\|}}{C}NH_2}{|}}{N}-\right]$$

These reactions are believed to go via the isothiocyanate route, e.g., $$HN=C=S + ROH \rightarrow H_2N-\overset{\overset{S}{\|}}{C}-OR$$

alkylthiocarbamate-(thiourethane)

The above representation is ideally presented with the understanding that various other reactions may occur.

The prime groups formed are
(1) substituted thioureas containing the following group $$-\overset{H}{N}-\overset{\overset{S}{\|}}{C}-\overset{H}{N}-$$

(2) Thio-biurets containing the following group $$-\overset{H}{N}-\overset{\overset{S}{\|}}{C}-\overset{H}{N}-\overset{\overset{S}{\|}}{C}-\overset{H}{N}-$$

(3) Thio-triurets containing the following group $$-\overset{H}{N}-\overset{\overset{S}{\|}}{C}-\overset{H}{N}-\overset{\overset{S}{\|}}{C}-\overset{H}{N}-\overset{\overset{S}{\|}}{C}-$$

(4) Thio-urethanes containing the following group $$-O-\overset{\overset{S}{\|}}{C}-NH-$$

(5) and combinations thereof.

The polyamines of this invention are oxyalkylated with any suitable oxyalkylation agent. Oxyalkylation is too well known to go into great detail. Typical oxyalkylation agents include those compounds containing $$\overset{\diagdown}{C}\underset{O}{-}\overset{\diagup}{C}$$

units such as ethylene oxide, propylene oxide, butylene oxide, etc., alone or in combination, added as mixtures thereof, sequentially added to form "blocks," etc.

In the thiourea reaction it is preferable to employ more moisture-free conditions than is employed with urea. Thus, the reaction contains a minimum of water.

The thioureylene reaction may be carried out over a wide temperature range provided the desired products are formed, for example from about 100° C. to 200° C., such as from about 115° to 185° C., but preferably from about 145° to 175° C.

The reaction time can vary widely depending on the particular reactants, the particular temperatures employed, the particular product desired, etc. Reaction time of about 6 to 15 hours, such as from about 8 to 12 hours, but preferably from about 7 to 10 hours.

The following are illustrative polyamines which can be employed in the invention.

The polyamines employed include those of the following formula:

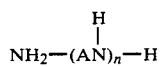

where n is for example 1–8 or greater, where A is a divalent radical, for example straight or branched

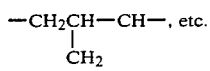

and m is for example 2–10 or greater. These include the following:

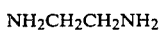

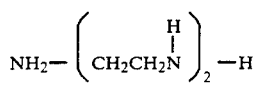

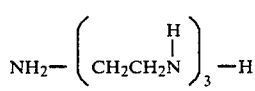

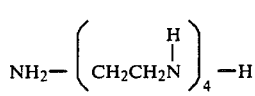

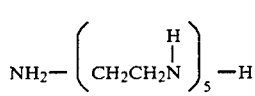

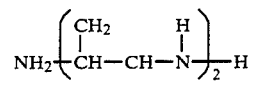

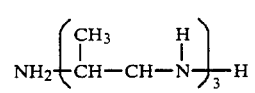

-continued

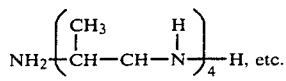

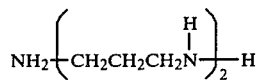

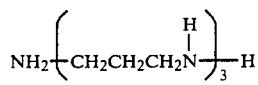

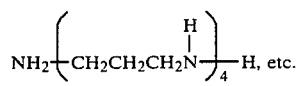

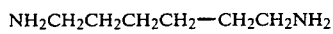

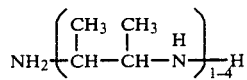

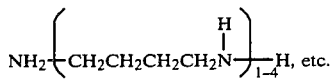

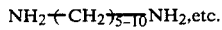

Other examples include the following alkylated polyamines for example of the formula

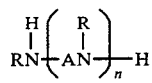

where the R's are H or a substituted group, such as cycloalkyl, alkyl, alkenyl, alkynyl, aryl, etc. The preferable type is of the formula

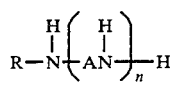

(R is straight chain or branch.)
Examples include the following:

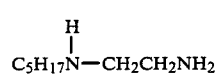

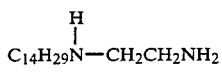

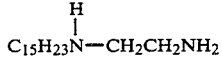

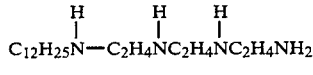

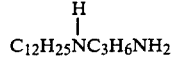

-continued

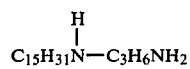

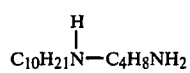

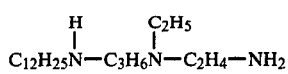

Other suitable amines are exemplified by:

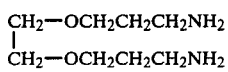

Aromatic polyamines can also be employed, for example:

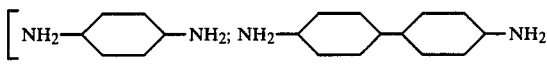

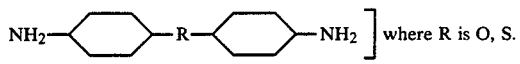

where R is O, S.

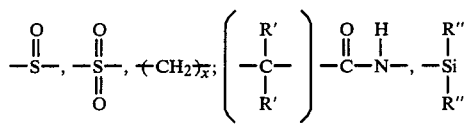

x = 1–4   where R' = H, Alkyl   where R" is alkyl

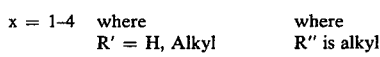

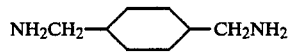

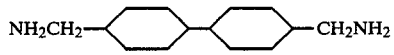

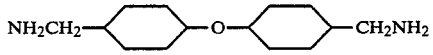

etc. or substituted derivatives thereof for example, alkyl, alkoxy, halo, etc. derivatives.

Thus, any polyamine capable of oxyalkylation, whether aliphatic, cyclo-aliphatic, aromatic, heterocyclic, etc., can be employed provided the oxyalkylated amine is capable of reacting with thiourea to form thioureylenes.

A convenient method of determining the amount of alkylene oxide to be added to the polyamine is based on reactive nitrogen-bonded hydrogen, i.e.

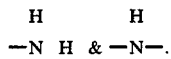

The replaceable hydrogen is encircled. Thus the primary amine group —NH$_2$ has two replaceable hydrogen and the secondary amino group

has one replaceable hydrogen. Thus if an amine has

| primary amine | 10.8% |
| secondary amine | 3.3% |
| tertiary amine | 1.0% | the NH equivalent is calculated as follows:

$$\frac{14}{10.8 \times 2 \, (NH_2) + 3.3 \times 1 \, (NH)} \times 100 =$$

g of EtO/NH equivalent $$\frac{14}{[10.8 \times 2] + [3.3 \times 1]} \times 100 = 56.22 \text{ g/NH equivalent.}$$

Thus, 56.22 g of amine and 44 g of ethylene oxide are reacted. This is sufficient to theoretically react with all the nitrogen bonded hydrogens. Since tertiary amines have no reactive hydrogens, they are not calculated. Since reaction of alkylene oxide is random or statistical, some hydrogens will be more reactive than others or alkylene oxides will tend to react with themselves to form —(CH$_2$CH$_2$O)$_n$H, so that not all hydrogen may be fully reacted by just employing an equivalent amount of ethylene oxide and an excess may have to be employed to fully replace all hydrogens.

Thus, the amount of alkylene oxide added per —NH— equivalents may vary widely, such as from about 0.1 mole per NH equivalents to about 3.0 moles per NH, for example from about 0.25 to 2.5 per NH equivalents, for example from about 0.35 to 1.5 per NH equivalents, but preferably from about 0.5 to 0.8 moles per NH equivalents.

After the amine is oxyalkylated it is analyzed for primary, secondary, and tertiary amines prior to reaction with urea.

The amount of thiourea reacted per NH equivalent of oxyalkylated amine may vary widely such as from about 0.1 mole per NH equivalent to about 3.0 moles of thiourea per NH equivalent, for example from about 0.25 to 2.5 moles of thiourea per NH equivalent, for example from about 0.35 to 1.5 moles of thiourea per NH equivalent, but preferably from about 0.5 to 0.8 moles per NH equivalent.

By employing the proper amount of thiourea in preparing thioureylene, one can control the solubility of the end product. For example, where thiourea is below about 0.30 equivalent per NH equivalent of oxyalkylated amine, the product is too soluble and where thiourea is above about 0.90 equivalent per NH equivalent of oxyalkylated amine, the product is too insoluble. Although thiourea outside this range is effective, it does not give optimum performance.

Prior to use as a flotation aid the thioureylene is converted to salt form to make it more water soluble. Thioureylene . HX where HX is an acid.

Any suitable acid may be employed whether inorganic, organic, or combinations thereof.

The anion derived from the acid which may vary widely may be for example, halide (Cl, Br, I, F), chlorates, carboxylates, such as derived from aliphatic acids, acetates, proprionates, aromatic acids, for example, benzoates, salicylates, phthalates, etc., phosphate, sulfate, sulfonate, etc. The salt is employed at a pH on the acid side, i.e., below about pH 7, such as from about 6.9 to 1.0, for example from about 6.9 to 3.0, but preferably from about 6.8 to 1.0, with an optimum of about 6.5 to 2.0.

In practice the HCl salt is employed.

The following examples are presented for purposes of illustration and not of limitation.

EXAMPLE IA

A sample of bis(hexamethylene) triamine (BHMT) was analyzed for its primary, secondary and tertiary amine content. The analysis yielded the following information:

| primary amine | 10.8% |
|---|---|
| secondary amine | 3.3% |
| tertiary amine | 1.0% |

The $NH_2$ equivalent was determined prior to the addition of oxide.

$NH_2$ equivalent = 1400/10.8% = 129.6 g/$NH_2$ eqt. based on primary amines only.

The amine is charged to a suitably outfitted reactor e.g., Chemco reactor model IPC-316-2AM, and heated to 70°–155° C. after which ethylene oxide is added. Oxide may be added to the extent that the all replaceable hydrogens have reacted with oxide moiety, e.g., as ideally represented by the following:

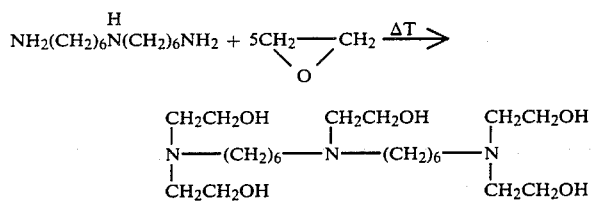

or any portion thereof. The oxide may also be added so that all reactable amine species are used to calculate the NH eqt., e.g.,

EXAMPLE IB $$\frac{1400}{\underbrace{(10.8 \times 2)}_{\text{primary amine}} + \underbrace{(3.3)}_{\text{secondary amine}}} = 56.22 \text{ g of amine/NH eqt of Example IA}$$
content content 44 g of ethylene oxide would have to be added to 56.22 g of Example IA to theoretically yield a molecule saturated with 2-hydroxyethanol groups. In the practice the oxide is added based on the $NH_2$ equivalent of the amine, since a fully saturated product would not yield the desired product, i.e., 88 g of ethylene oxide to 112.44 amine.

EXAMPLE IC 129.6 g of Example IA was reacted with 40 g of ethylene oxide, to yield a partially oxide-modified amine containing random statistically scattered (e.g., 2-hydroxyl ethanol groups) about the molecule leaving substantial NH and $NH_2$ groups available for the subsequent reaction with thiourea.

The oxyethylated product was then analyzed to yield the following primary, secondary and tertiary amine analysis, as indicated in oxyalkylated Product A:

| Oxyalkylated Product A | |
|---|---|
| Primary amine | 3.66% |
| Secondary amine | 2.83% |
| Tertiary amine | 4.34% |

This product was then reacted with thiourea at the NH equivalency indicated in the following examples.

Thioureylene Example I 137.93 g (1 NH equivalent of oxyalkylated Product A)
38.06 g thiourea (one equivalent)

Oxyalkylated Product A and thiourea were heated while stirring 135°–200° C. in a three neck reaction flask outfitted with a condenser Dean/Stark trap stirring and heating apparatus. The reaction set-up was preweighed before reaction. The reaction was continued for 5–21 hours after which the reaction set-up was weighed again to determine its weight loss due to the loss of ammonia and the decomposition products of thiourea. This product was a viscous wax-like substance mostly water insoluble. This product was diluted with appropriate solvents, then reacted with an acid from the group but not limited to, HCl, acetic, sulfuric which renders the product soluble to dispersable in water.

Thioureylene Example IIA 137.93 g (1 NH equivalent of oxyalkylated Product A)
26.64 g of thiourea (0.70 NH equivalent)

was reacted in a similar fashion to Thioureylene Example I and formulated as follows:

Formulated Example IIA 100 g of Thioureylene of Example IIA
50 g water
50 g HCl (20° Be)
10 g 2-propanol.

Thioureylene Example IIIA 137.93 g of oxyalkylated Product A
24.74 g thiourea (0.65 NH equivalent).

Formulated Example IIIA

The product of Thioureylene Example IIIA was formulated as follows:
100 g of Thioureylene Example IIIA
55 g water
45 g HCl 20% Be
12 g 2-propanol.

These products were water soluble products useful as an aid to removal of crude oil and other particulate matter from oilfield production water in conjunction with a mechanical device, e.g., WEMCO Depurator, an air flotation apparatus and or dissolved air flotation device.

Oil-in-Water Demulsification

This phase of the invention relates to a process for resolving or separating emulsions of the oil-in-water class, by subjecting the emulsion to the action of certain chemical reagents.

Emulsions of the oil-in-water class comprise organic oily materials, which, although immiscible with water or aqueous or non-oily media, are distributed or dispersed as small drops throughout a continuous body of non-oily medium. The proportion of dispersed oily material is in many and possibly most cases a minor one.

Oil-field emulsions containing small proportions of crude petroleum oil relatively stably dispersed in water or brine are representative oil-in-water emulsions. Other oil-in-water emulsions include: steam cylinder emulsions, in which traces of lubricating oil are found dispersed in condensed steam from steam engines and steam pumps; oil-in-water emulsions occurring in the cooling water systems of gasoline absorption plants; emulsions of petroleum residues-in-diethylene glycol, in the dehydration of natural gas, etc.

In other industries and arts, emulsions of oily materials in water or other non-oily media are encountered, for example, in sewage disposal operations, milk and mayonnaise processing, marine ballast water disposal. In cleaning the equipment used in processing such products, diluted oil-in-water emulsions are inadvertently, incidentally, or accidentally produced. The disposal of aqueous wastes is, in general, hampered by the presence of oil-in-water emulsions.

Steam distillation and other production procedures sometimes cause oil-in-water emulsions to be produced, from which the valuable oils are difficultly recoverable.

In all such examples, a non-aqueous or oily material is emulsified in an aqueous or non-oily material with which it is naturally immiscible. The term "oil" is used herein to cover broadly the water-immiscible materials present as dispersed particles in such systems. The non-oily phase obviously includes diethylene glycol, aqueous solutions, and other non-oily media in addition to water itself.

Among the most important emulsions of non-saponifiable material in water are petroleum oil-in-water emulsions.

Oil-in-water emulsions contain widely different proportions of dispersed phase. Where the emulsion is a waste product resulting from the flushing with water of manufacturing areas or equipment, the oil content may be only a few parts per million. Naturally-occurring oil-field emulsions of the oil-in-water class carry crude oil in proportions varying from a few parts per million to about 20%, or even higher in rare cases.

The present invention is concerned with the resolution of those emulsions of the oil-in-water class which contain a minor proportion of dispersed phase, ranging from 20% down to a few parts per million.

Although the present invention relates to emulsions containing as much as 20% dispersed oily material, many if not most of them contain appreciably less than this proportion of dispersed phase. In fact, most of the emulsions encountered in the development of this invention have contained about 1% or less of dispersed phase. It is to such oil-in-water emulsions having dispersed phase volumes of the order of 1% or less to which the present process is particularly directed. This does not mean that any sharp line of demarcation exists, and that, for example, an emulsion containing 1.0% of dispersed phase will respond to the process, whereas one containing 1.1% of the same dispersed phase will remain unaffected; but that, in general, dispersed phase proportions of the order of 1% or less appear most favorable for application of the present process.

The present process, as stated above, appears to be effective in resolving emulsions containing up to about 20% of dispersed phase. It is particularly effective on emulsions containing not more than 1% of dispersed phase, which emulsions are the most important, in view of their common occurrences.

Some emulsions are by-products of manufacturing procedures in which the composition of the emulsion and its ingredients is known. In many instances, however, the emulsions to be resolved are either naturally-occurring or are accidentally or unintentionally produced; or in any event they do not result from a deliberate or premeditated emulsification procedure. In numerous instances, the emulsifying agent is unknown; and as a matter of fact an emulsifying agent, in the conventional sense, may be felt to be absent. It is obviously very difficult or even impossible to recommend a resolution procedure for the treatment of such latter emulsions, on the basis of theoretical knowledge. Many of the most important applications of the present process are concerned with the resolution of emulsions which are either naturally-occurring or are accidentally, unintentionally, or unavoidably produced. Such emulsions are commonly of the most dilute type, containing about 1% or less of dispersed phase, although concentrations up to 20% are herein included, as stated above.

The process which constitutes the present invention consists in subjecting an emulsion of the oil-in-water class to the action of a reagent of the kind herein described, thereby causing the oil particles in the emulsion to coalesce sufficiently to rise to the surface of the non-oily layer (or settle to the bottom, if the oil density is greater), when the mixture is allowed to stand in the quiescent state after treatment with the reagent or demulsifier.

Applicability of the present process can be readily determined by direct trial on any emulsion, without reference to theoretical considerations. This fact facilitates its application to naturally-occurring emulsions, and to emulsions accidentally, unintentionally, or unavoidably produced; since no laboratory experimentation, to discover the nature of the emulsion components or of the emulsifying agent, is required.

The demulsifying agents herein described for resolution of oil-in-water type emulsions may be used alone or in combination with other products which also are effective for resolution of oil-in-water emulsions, for example, in combination with electrolytes.

Examples of electrolytes which were found to be suitable are: $FeCl_3$, $ZnCl_2$, $Al_2(SO_4)_3$, $AlCl_3$, etc.

The present reagents are useful, because they are able to recover the oil from oil-in-water-class emulsions more advantageously and at lower cost than is possible using other reagents or other processes. In some instances, they have been found to resolve emulsions which were not economically or effectively resolvable by any other known means.

The reagents may be employed alone, or they may in some instances be employed to advantage admixed with other and compatible oil-in-water demulsifiers.

The process is commonly practised simply by introducing small proportions of reagent into an oil-in-water-class emulsion, agitating to secure distribution of the reagent and incipient coalescense, and letting stand until the oil phase separates. The proportion of reagent required will vary with the character of the emulsion to be resolved. Ordinarily, proportions of reagent required are from 1/5,000 to 1/500,000 the volume of emulsion treated; but more is sometimes required.

In some instances, importantly improved results are obtained by adjusting the pH of the emulsion to be treated, to an experimentally determined optimum value.

The reagent feed rate also has an optimum range, which is sufficiently wide, however, to meet the tolerances required for the variances encountered daily in commercial operations. A large excess of reagent can produce distinctly unfavorable results.

The manner of practicing the present invention is clear from the foregoing description.

The reagents of this invention are useful in the clarification of water containing emulsified oil or suspended oil and/or oily solids. The application is especially effective for the resolution of oil-in-water emulsions as encountered in oil fields, oil-in-water emulsions resulting from refinery processes and emulsions of cutting and rolling oils from metal working industries. The reagent may be used in simple settling tanks or basins.

The compositions of this invention are employed as reagents in removing oils, solids, and combinations thereof from aqueous systems. They are particularly effective as such a reagent in flotation systems.

Removal of Oils and Solids from Aqueous Systems

In the present process, to remove oils, or solids, or combinations thereof, from aqueous systems, the reagent is introduced at any convenient point in the system, and it is mixed with the oils or solids in any desired manner, such as by being pumped or circulated through the system or by mechanical agitation such as paddles or by gas agitation. After mixing, the mixture of oils or solids and reagent is allowed to stand quiescent until the constituent phases of the emulsion separate. Settling times and optimum mixing times will, of course, vary with the nature of the oil or solid and the apparatus available. The operation, in its broadest concept, is simply the introduction of the reagent into the oils or solids, the mixing of the two to establish contact and promote coalescence, and, usually, the subsequent quiescent settling of the agitated mixture, to produce the aqueous and non-aqueous phases as stratified layers.

Agitation may be achieved in various ways. The piping system through which the oil- or solids-containing system is passed during processing may itself supply sufficient turbulence to achieve adequate mixing of reagent and system. Faffled pipe may be inserted in the flow sheet to provide agitation. Other devices such as perforated-chamber mixers, excelsior- or mineral- or gravel- or steel-shaving-packed tanks, beds of stones or gravel or minerals in open ducts or trenches may be employed beneficially to provide mixing. The introduction of a gas, such as natural gas or air, into a tank or pipe in which or through which the mixture of reagent and system is standing or passing is frequently found suitable to provide desired agitation.

It has been found that the factors, reagent feed rate, agitation, and settling time are somewhat interrelated. For example, with sufficient agitation of proper intensity the settling time required can be materially shortened. On the other hand, if agitation is relatively non-procurable but extended settling time is, the process may be equally productive of satisfactory results. The reagent feed rate has an optimum range, which is sufficiently wide, however, to meet the tolerances required for the variances encountered daily in commercial operations.

Application of a suitable gas in a procedure approximating that of the froth flotation cell employed in ore beneficiation, after the present reagent has been added to the system to be resolved, frequently has a favorable influence of totally unexpected magnitude. By incorporating the step of subjecting the chemicalized (i.e., containing the reagent) system to the action of air in a sub-aeration type flotation cell, a clear aqueous layer is sometimes obtained in a matter of seconds, without added quiescent settling and with approximately as much reagent. Natural gas was found to be as good a gaseous medium as was air, in this operation.

It should be distinctly understood that such aeration technique, while an important adjunct to the use of the present reagent, in some cases, is not an equivalent procedure. This may be proved by subjecting an un-chemicalized system to aeration for a period of minutes without detectable favorable effect. Addition of the reagent to such aerated system will produce resolution, promptly.

The details of the mechanical structures required to produce aeration suitable for the present purpose need not be given here. It is sufficient to state that any means capable of producing small gas bubbles within the body of the system is acceptable for use.

The flotation principle has long been employed in the beneficiation of ores. Many patents in this art illustrate apparatus suitable for producing aeration of liquids. Reference is made to Taggart's "Handbook of Ore Dressing," which describes a large number of such devices.

Suitable aeration is sometimes obtainable by use of the principle of Elmore, U.S. Pat. No. 826,411. In that ore beneficiation process, an ore pulp was passed through a vacuum apparatus, the application of vacuum liberating very small gas bubbles from solution in the water of the pulp, to float the mineral. A more recent application of this same principle is found in the Door "Vacuator."

The manner of practicing the present invention using aeration is clear from the foregoing description.

The order in which the reagent and the aeration step are applied is relatively immaterial. Sometimes it is more convenient to chemicalize the system and subsequently to apply the aeration technique. In others, it may be more advantageous to produce a strongly frothing system and then introduce the reagent into such aerated system.

Any desired gas can be substituted for air. Other commonly suitable gases include natural gas, nitrogen, carbon dioxide, oxygen, etc., the gas being used essentially for its levitation effect. If any gas has some deleterious effect on any component of the system, it will obviously be desirable to use instead some other gas which is inert under the conditions of use.

The amount of thioureylene reagent used will vary depending on the particular thioureylene, the particular system, etc. In general, the amount of thioureylene employed in the system is at least about 0.5 ppm, such as from about 1.0 to 60 ppm, for example from about 5 to 40 ppm, but preferably from about 3.0 to 30 ppm. Larger amounts may be used but there is generally no cost/performance reason for so doing.

WEMCO Depurator Flotation Machine is a flotation machine for removal of emulsified oily wastes and suspended solids from petroleum industry wastewater.

The WEMCO Depurator unit employs mechanically-induced air flotation to separate solids, oils, or organic materials from refinery or oil field effluent in larger volumes, in less space, and at lower cost than any other machine. It can clean large quantities of wastewater containing from 200 to 5,000 ppm of oil, depending on the type of oil and emulsion. In most applications, less than 10 ppm of oil remain after a four-minute cleaning cycle.

It is available in a variety of sizes to handle from 1,720 to 171,000 barrels of wastewater per day. Depurator machines can be installed at costs 15–40% less than other comparable flotation equipment. Maintenance costs are lower, too. The Depurator unit also requires at least 50% less space than comparable equipment for its volume capacity. Over 300 successful field installations to date.

WEMCO Depurator units are composed of four standard WEMCO flotation cells. Each cell is equipped with a motor-driven self-aerating rotor mechanism. As the rotor spins, it acts as a pump, forcing water through a disperser and creating a vacuum in the standpipe. The vacuum pulls gas into the standpipe and thoroughly mixes it with the wastewater. As the gas/water mixture travels through the disperser at high velocity, a shearing force is created, causing the gas to form minute bubbles. Oil particles and suspended solids attach to the gas bubbles as they rise to the surface. The oil and suspended solids gather in a dense froth on the surface, are removed from the cell by skimmer paddles and collected in external launders.

In the majority of applications, natural gas or nitrogen is used to form the bubbles. The absence of oxygen prevents the growth of harmful bacteria and also reduces downstream corrosion. A pressure of 0.50 to 1.0 ounce maintains a gas blanket between the liquid level and gas-tight cover. When air is used, it is induced by the Depurator machine at atmospheric pressure. Self-induced mechanical air flotation eliminates need for auxiliary air compressors or blowers.

Processing is often improved with the aid of a chemical injected into the water upstream from the float cell. These compounds break oil-in-water emulsions, gather suspended solids, and stabilize the air bubbles to promote froth flotation.

The Depurator machine consists of a self-supporting, all-steel skid-mounted tank, with integral float-collecting flumes and gas-tight covers. Tank interior is high-temperature epoxy coated for greatest corrosion resistance. Inspection doors are provided on both sides of the tank, plus a breather valve and pneumatic liquid level controller.

Each standpipe is equipped with gas intake ports beneath the gas-tight cover. A separate motor powers each rotor/disperser mechanism. Two ¼ horsepower gearmotors drive the skimmer assemblies. All motors are explosion-proof, 3 phase, 60 cycle, 230/460 volt.

The following are the major petroleum industry applications.

Oil Field Production Water

The Depurator machine wrings almost the final drops of oil from produced water. After initial treatment by gravity oil/water separators, such as free water knockouts, gun barrels, and skim tanks, oilfield water can be terminally cleaned to most community and company standards by the WEMCO Depurator machine. Depurator units will remove the emulsified oil left by preliminary water treatment which could prevent formation plugging and reduce pump efficiency when the water is to be reinjected for water flooding. For steam flooding, the Depurator unit is used ahead of boiler pretreatment equipment.

If the wastewater is to be disposed of by percolation ponds, or returned to existing waterways, the Depurator machine has consistently proven its ability to clean the water to local, state and federal standards.

Refinery Process Water

At the refinery, the Depurator wastewater treatment generally follows gravity oil-water separation. The wastewater includes process water from desalters, tank and water drawoffs, steam stripping condensate, pump gland cooling, barometric condenser, treating plant wash, caustic treatment, and loading facility washdown. It may also include storm run-off water.

The Depurator device is first choice for secondary wastewater treatment because, unlike gravity oil-water separators, it will break emulsions with appropriate chemical additives. More than a dozen successful installations are currently in refinery operation.

Petrochemical Wastewater

Wastewater created in the production of bulk chemicals derived from natural gas or petroleum is often distinguished from the usual oil refinery product by special characteristics. No single oil/water separation method has proven capable of handling all the compounds produced. The flotation process, as employed by the WEMCO Depurator machine, has proven to be the best wastewater treatment for many of these oils and suspended solids. Bench tests are recommended for each specific application.

The following Field Examples are presented for purposes of illustration and not of limitation.

FIELD EXAMPLE I

At a location in West Texas a WEMCO Depurator is used to remove residual oil from oilfield production water prior to its reinjection into the ground (secondary recovery). The WEMCO Depurator without the aid of a chemical additive of the invention exhibited the following efficiency towards removing the residual oil from the production water:
WEMCO inlet water (influent) 310 ppm
WEMCO outlet water (effluent) 285 ppm
representing 8.1% efficiency. Adding 3–12 ppm of Formulated Example IIA injected into the influent exhibited the following: 295 ppm influent, 32 ppm effluent, 89.2% efficiency. The chemical was removed and the effluent contaminant level increased and the efficiency of the oil removal dropped to 34.2%, 287 ppm influent, 189 ppm effluent. At a location in Wyoming a WEMCO unit was operating at 72% efficiency, 336 ppm influent, 93 ppm effluent; 3–5 ppm of Formulated Example IIA increased the efficiency 322 ppm influent, 12 ppm effluent, 96.3% efficiency.

FIELD EXAMPLE II

A WEMCO Depurator processing oilfield production water at a West Texas location had an oily contamination of 380 ppm influent and 187 ppm effluent. This stream was treated ahead of the inlet side of the WEMCO with 10–12 ppm of Formulated Example IIA. This treatment reduced the effluent oil count to 10–23 ppm.

FIELD EXAMPLE III

A WEMCO Depurator operating in Bakersfield, Calif. was processing oilfield production water. The influent was between 160–180 ppm oil, the effluent was 52–68 ppm. The influent stream was treated with 6 ppm of Formulated Example IIA which reduced the effluent oil count to 9–12 ppm.

FIELD EXAMPLE IV

Another WEMCO Depurator operating in West Texas processing oilfield production water was treated with Formulated Example IIIA. The oil count ran 286 ppm influent, 198 ppm effluent. Treating the influent stream with 12 ppm of Formulated Example IIIA reduced the effluent oil to 14 ppm.

These products have the ability to attract oil and aiding in its removal from the flotation apparatus. In addition to their apparent ability to attract oil, they also generate a froth that is beneficial towards the removal of the residual oil. Frothing action alone is not satisfactory. The solubility of the end reaction product is also important. Thioureylenes of the type shown in Examples IIA and IIIA where the thiourea weight was below 23 g or above 75 g are respectively too soluble and too insoluble respectfully based on an NH equivalent of the modified amine but these products still exhibit activity. Therefore the compositions of this invention should have the desired solubility and chemical characteristics after the addition of acids to the desired pH so as to obtain the desired solubility.

FIELD EXAMPLE V

The Thioureylenes of Formulated Examples 1A, 1B and 1C also exhibit utility as reverse, i.e. O/W demulsifiers of oilfield as well as industrial oil-in-water/water-in-oil demulsifiers. They are typically tested in the following fashion.

A series of milk dilution bottles having a volume capacity of 150 ml outfitted with a screw cap, are filled to the 100 ml mark with test solution, e.g., oilfield oil-in-water emulsion. Experimental reverse demulsifiers are injected into each bottle of a series of bottles—in increasing amounts, e.g., 2, 4, 6, 8, 10 ppm or e.g., 5, 10, 15, 20, etc.; the bottles are agitated by shaking said bottles, e.g., for 25, 50, 100, 200 shakes, etc. after which the bottles are observed to determine whether the chemical or chemicals being investigated are effective toward separating the oil and/or particulate matter from the water. The oil usually floats to the top of the water layer and the effectiveness of the chemical is judged by the clarity of the water layer.

Formulated Examples 1A, 1B and 1C are effective as reverse, i.e. O/W demulsifiers for petroleum.

The term "particulate matter" in the claims includes any matter in small unit form such as solids, liquids, combinations thereof, etc.

I claim:

1. The process of removing particulate matter from an aqueous system which comprises treating said system with a thioureylene derived from reacting an oxyalkylated polyamine with thiourea.

2. The process of claim 1 wherein said polyamine is an alkylene polyamine.

3. The process of claim 2 wherein said polyamine is an alkylene diamine.

4. The process of claim 1 wherein said oxyalkylated polyamine is an oxyethylated polyamine.

5. The process of claim 2 wherein said oxyalkylated alkylene polyamine is an oxyethylated alkylene polyamine.

6. The process of claim 1 wherein flotation is employed.

7. The process of claim 2 wherein flotation is employed.

8. The process of claim 3 wherein flotation is employed.

9. The process of claim 4 wherein flotation is employed.

10. The process of claim 5 wherein flotation is employed.

11. The process of claim 1 wherein the particulate matter comprises an emulsion.

12. The process of claim 2 wherein the particulate matter comprises an emulsion.

13. The process of claim 3 wherein the particulate matter comprises an emulsion.

14. The process of claim 4 wherein the particulate matter comprises an emulsion.

15. The process of claim 5 wherein the particulate matter comprises an emulsion.

* * * * *